United States Patent [19]  
Cama et al.

[11] 4,267,188  
[45] May 12, 1981

[54] 5-SUBSTITUTED-1-CARBA-PEN-2-EM-3-CARBOXYLIC ACID

[75] Inventors: Lovji D. Cama, Cresskill; Burton G. Christensen, Scotch Plains, both of N.J.

[73] Assignee: Merck & Co., Inc., Rahway, N.J.

[21] Appl. No.: 65,306

[22] Filed: Aug. 9, 1979

[51] Int. Cl.³ .................... G07D 487/04; A61K 31/40
[52] U.S. Cl. .............................. 424/274; 265/239 A; 265/245.2 T; 424/250; 424/263; 424/269; 424/270; 424/273 R; 424/273 P; 544/405; 546/272
[58] Field of Search ................ 268/245.2 T; 429/274; 546/272

[56] References Cited  
U.S. PATENT DOCUMENTS 4,153,714  5/1979  Ponsford ............................ 424/274

Primary Examiner—Mary C. Lee

Attorney, Agent, or Firm—Frank M. Mahon; James A. Arno; Julian S. Levitt

[57] ABSTRACT

Disclosed are 1-carba-pen-2-em-3-carboxylic acids of the following structure:

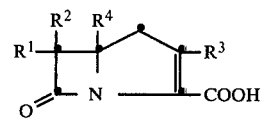

wherein $R^1$, $R^2$, $R^3$ and $R^4$ are, inter alia, independently selected from the group consisting of hydrogen ($R^4$ is not hydrogen), alkyl, aryl, and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

32 Claims, No Drawings

5-SUBSTITUTED-1-CARBA-PEN-2-EM-3-CARBOXYLIC ACID

BACKGROUND OF THE INVENTION

This invention relates to substituted 1-carba-pen-2-em-3-carboxylic acids which are useful as antibiotics and which may be represented by the following generic structural formula (I):

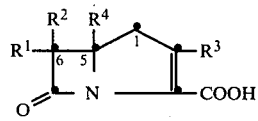

wherein $R^1$, $R^2$, $R^3$ and $R^4$ are independently selected from the group consisting of hyrogen ($R^4$ is not H), substituted and unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl and heterocyclylalkyl wherein the substituent or substituents relative to the above named radicals are selected from the group consisting of amino, hydroxy, alkoxyl, mercapto, alkylthio, arylthio, sulfamoyl, amidino, guanidino, nitro, chloro, bromo, fluoro, cyano and carboxy; and wherein the hetero atom in the above-named heterocyclic moiety is selected from the group consisting of oxygen, nitrogen and sulphur.

This invention also relates to the pharmaceutically acceptable salt, ester and amide derivatives of the compounds of the present invention identified by structure I, above.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

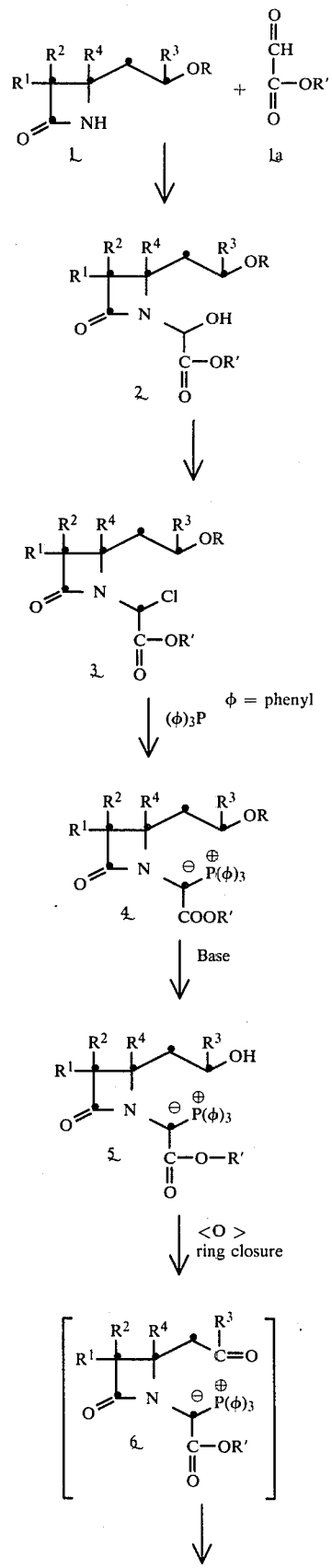

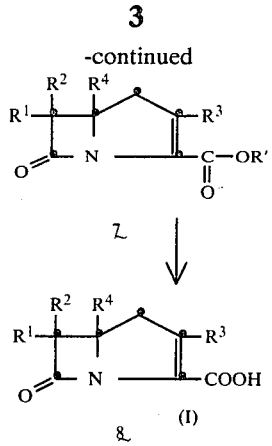

wherein R[1], R[2], R[3] and R[4] are as defined; R and R' are readily removable blocking groups; R' may also be a pharmaceutically acceptable ester moiety. Typically, the blocking group R is an acyl such as a lower alkanoyl, aralkylcarbonyl or the like such as acetyl, bromo-t-butoxycarbonyl, benzyloxycarbonyl, formyl, trifluoroacetyl and the like or a trialkylsilyl such as trimethylsilyl or t-butyl dimethylsilyl group; and typically the blocking group R' is substituted or unsubstituted alkyl, aralkyl, alkenyl, or the like such as benzyl, p-nitrobenzyl, o-nitrobenzyl, pivaloyloxymethyl, bromo-t-butyl and the like.

In words relative to the above reaction diagram, a suitably substituted azetidinone (1) is reacted with a glyoxalate ester such as benzyl glyoxalate to form the corresponding 1-(benzyloxycarbonylhydroxymethyl) azetidinone (2). The reaction 1→2 is conveniently carried out in a solvent such as benzene, toluene, xylene and the like at a temperature of from about 25° C. to reflux for from 2 to 10 hours. There is no criticality as to the precise identity of the solvent, provided only that it adequately solubilizes the reactants and be inert or substantially inert to the desired course of reaction. The halogenation reaction 2→3 may be conducted by any of a variety of well-known halogenation means. Suitable reagents include: $SOCl_2$, $POCl_3$, oxalyl chloride and the like. A preferred means of chlorination involves treating 2 in a solvent such as tetrahydrofuran (THF), ether, $CH_2Cl_2$ and the like with thionylchloride in the presence of 1 to 2 equivalents (relative to the thionylchloride) of a base such as pyridine, triethylamine, quinoline and the like. Typically, the reaction is conducted at a temperature of from −30° to 25° C. for from 0.5 to 1 hour. The resulting 1-(benzyloxycarbonylchloromethyl)-azetidinone species, 3, is isolated, if desired, by conventional procedures for later reaction, 3→4. The intermediate 4 is prepared from 3 by treating 3 in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)-phosphine or the like. Typically the reaction is conducted under a nitrogen atmosphere at a temperature of from −20° to 25° C., for from 0.5 to 2 hours. The reaction 4→5 may be achieved by any of a variety of well-known deblocking procedures such as hydrolysis or hydrogenolysis. A particularly convenient means for the deblocking, 4→5, is by an alcoholysis procedure comprising treating 4 in a lower alkanol such as methanol, ethanol, or the like in the presence of 0.1 to 1.4 equivalents of the corresponding alkali metal alkoxide such as sodium methoxide or the like; typically the reaction is conducted at a temperature of from 0° to 25° C., for from 0.5 to 2 hours. The ring closure reaction 5→7 proceeds via the oxo intermediate 6 and is achieved by treating 5 with an equivalent of an oxidizing system such as 1:1 mixture of dimethylsulfoxide (DMSO) and acetic anhydride ($Ac_2O$); other oxidizing systems include cyclohexylcarbodiimide in DMSO, and $CrO_3.2$(pyridine) in $CH_2Cl_2$, for example. Typically, the closure step 5→7 is conducted at a temperature of from about 0° to 100° C. for from 0.25 to 24 hours in the oxidative system (DMSO/$Ac_2O$) described above or by heating from 100°–160° C. (after isolation of the oxo compound 6) in a solvent such as benzene, toluene, dioxane, xylene, or DMF. The carboxyl deblocking step 7→8 may be achieved by a number of well-known procedures such as hydrolysis, hydrogenation, or photolysis of a suitable R' group. Suitable hydrogenation catalysts for deblocking include the platinum metals and their oxides such as palladium on carbon and the like; suitable solvents for the hydrogenation include methanol, dioxane/$H_2O$, ethanol/$H_2O$ and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

The glyoxalate esters 1a used to react with 1 can be prepared by oxidation of the corresponding tartaric acid diesters with oxidants such as periodic acid or lead tetraacetate in a solvent such as THF, benzene or methylene chloride at −20° to 25° for ¼ to 4 hrs. The tartarate esters are prepared from dilithio tartarate or disodio tartarate by reaction with R'X wherein X is chloro, bromo or iodo and R' is as defined above in a solvent such as DMF or DMSO at 25° to 70° C. for from 4 to 48 hrs. As noted above, R' may be a pharmaceutically acceptable ester moiety. Such pharmaceutically acceptable esters and amides, however, may also be prepared from the free acid of I according to the procedure of co-pending U.S. Patent Application Ser. No. 733,651 filed Oct. 18, 1976, now abandoned which is directed to the pharmaceutically acceptable esters and amides of thienamycin and their preparation. Accordingly, for its disclosure relative to such pharmaceutically acceptable forms and their means of preparation, the above-cited application is incorporated herein by reference. The following diagram summarizes the synthesis of the substituted azetidinones starting material, 1.

Preparation of 1:

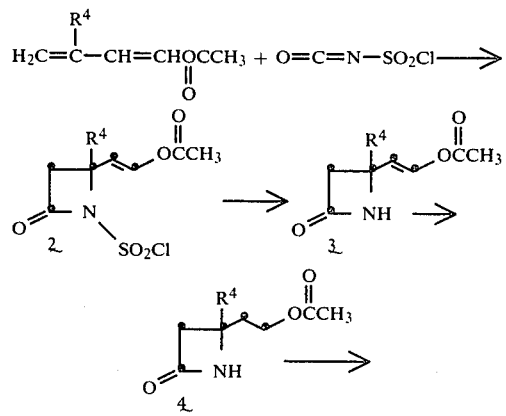

Preparation of 1:
-continued

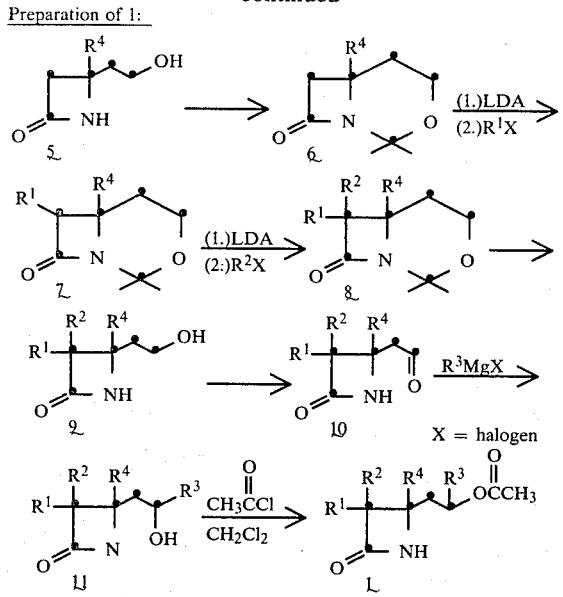

In words relative to the above diagram for the preparation of 1, the 4-(2-acetoxyvinyl)azetidine-2-one (3) is prepared by reacting chloro sulphonyl isocyanate and an appropriately substituted acyloxybutadiene in a solvent such as anhydrous dimethyl ether at a temperature of from about −30° C. to 0° C. under a nitrogen atmosphere. (Such substituted acyloxybutadienes are either known or prepared by known procedures. The reaction intermediate 2 is converted to 3 by hydrolysis. The reduction of 3 to provide the 4-(2-acetoxyethyl)-2-azetidinone (4) is conducted by any convenient means such as hydrogenation in the presence of a catalyst such as platinum, palladium or oxides thereof under a hydrogen pressure of from 1 to 20 atmospheres in a solvent such as ethanol, ethylacetate, or the like at a temperature of from 0° to 25° C., for from 5 minutes to 1 hour. The 4-(2-hydroxyethyl)-2-azetidinone species, 5, is obtained from 4 by hydrolysis. The 8-oxo-2,2-dimethyl-3-oxa-1-azabicyclo-[4.2.0]octane species, 6, is obtained on treatment of 5 with 2,2-dimethoxypropane in the presence of a catalyst such as boron trifluoride etherate in a solvent such as methylene chloride at a temperature of from 0° to 40° C. for from 1 to 40 minutes. Alternatively, 5 can be treated with boron-trifluoride etherate and trimethylorthoformate to give 8-oxo-2-methoxy-3-oxa-1-azabicyclo[4.2.0]octane which can be mono- or dialkylated following the procedures for 6→7 or 8. Alkylation of 6 provides 7. Typically, 6 is treated with a strong base such as lithium diisopropyl amide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, $R^1X$, is added ($R^1$ is as described above and X is chloro or bromo; alternatively the alkylating agent may be $R^1$-tosylate, $R^1$-mesylate or an aldehyde or ketone such as acetaldehyde and the like) to provide mono- alkylated species 7. When desired dialkylated species 8 may be obtained from 7 by repeating the alkylating procedure, 6→7. Species 9 is obtained from 7 or 8 by acid hydrolysis. Oxidation of 9 with an oxidizing agent such as DMSO-acetic anhydride, pyridine.$CrO_3$, cyclohexylcarbodiimide/DMSO, and the like in a solvent such as DMSO, pyridine, acetonitrile, methylene chloride, and the like at a temperature of from about 0° to 25° C. for from 0.5 to 12 hours provides 10 which upon treatment with the Grignard reagent $R^3MgX$ ($R^3$ is as defined above and X is halogen) provides 11. Typically, the alkylation reaction 10→11 is conducted in a solvent such as ether, THF, benzene and the like at a temperature of from −78° to about 25° C. for from 0.5 to about 24 hours.

The desired blocked-species 1 is obtained by treating 11 with an acylating agent such as acetyl chloride, formic acetic anhydride, trifluoroacetic anhydride and the like in a solvent such as $CH_2Cl_2$, $CHCl_3$, THF and the like at a temperature of from −20° to about 25° C. for from 0.5 to about 4 hours. The starting material 1 may be isolated for later reaction in accordance with the procedures of the present invention for the preparation of the compounds of the present invention.

It should be noted that in the establishment of $R^3$ (9→10→11), the ring nitrogen may be protected by an easily removable blocking group R":

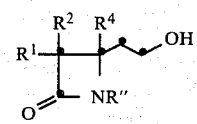

wherein R" is acyl or triorganosilyl such as trimethylsilyl, t-butyldimethylsilyl, trifluoroacetyl, formyl, or the like. Removal of R" is accomplished by hydrolysis to provide 11 (or 1 from N-blocked 1) according to well-known procedures.

Starting material 1, may alternatively be prepared by the following scheme:

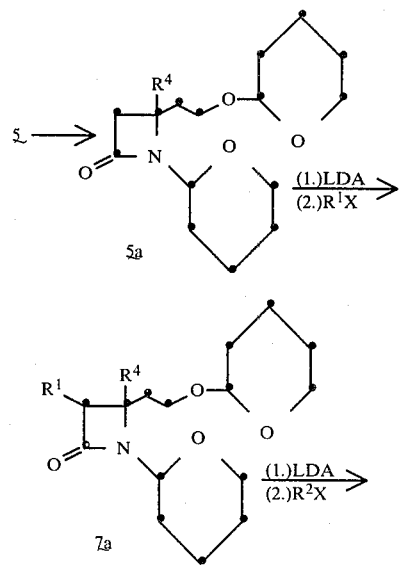

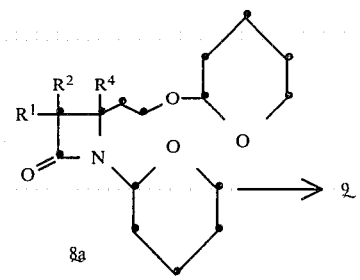

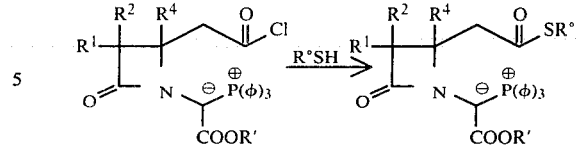

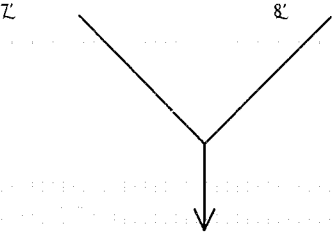

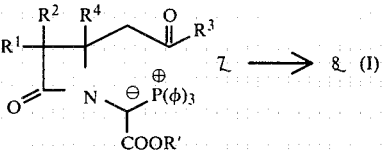

wherein all symbolism is as previously defined.

Reaction 5→5a is accomplished by treating 5 with 2,3-dihydropyran in a solvent such as p-dioxane, benzene, and the like in the presence of p-toluene sulphonic acid, perchloric acid, or the like at a temperature of from 0° to about 30° C. The intermediate 5a may be isolated for later alkylation to obtain 7a and 8a by procedures analogous to previously described reactions 6→7→8. Intermediate species 9 is obtained from 7a or 8a by mild acid hydrolysis.

Finally, it should be noted that intermediate species 9 may conveniently be prepared for later reaction in the above scheme by internal acylation according to the following reaction:

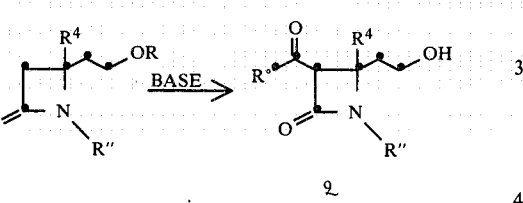

wherein R is acyl,

is $R^1$ and $R°$ is for example lower alkyl, acyl, or the like. Typically the above reaction is conducted in a solvent such as tetrahydrofuran, ether, dimethoxyethane, or the like in the presence of 1 to 2 equivalents of a strong base such as lithium diisopropylamide, sodium hydride, potassium hydride or the like at a temperature of from −78° to 25° C., for from 0.5 to 24 hours.

An alternate procedure for establishing the 2-substituent, $R^3$, in the total synthesis of I may be illustrated by the following reaction diagram:

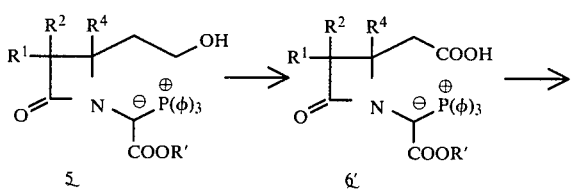

In words relative to the above diagram, species 5 is the same as that shown in the first-described reaction diagram except that $R^3$ is hydrogen. This species, 5, is oxidized to yield 6'. Any of a variety of oxidizing systems may be employed such as Jones' Reagent, $KMnO_4$, $Ag_2O$, and the like in solvents such as acetone, aqueous THF, aqueous dioxane, and the like at a temperature range of from 0° to 25° C. for from 10 min. to 24 hours. The preferred conditions of oxidation, 5→6', comprise treating 5 in a solvent such as acetone, or the like with Jones' Reagent at a temperature of from 0° to 25° C. for from 10 min. to 0.5 hours. Chlorination of 6' yields 7'. Typically the chlorination is accomplished by treating 6' in a solvent such as $CH_2Cl_2$, THF, $Et_2O$, $CHCl_3$, $C_6H_6$, or the like with a chlorinating agent such as oxalyl chloride, $SOCl_2$, $POCl_3$, or the like at a temperature of from −20° to 25° C. for from ½ to 24 hours. Treating 7' with a mercaptan in R°SH such as phenyl mercaptan, butyl mercaptan, ethyl mercaptan, p-nitrophenyl mercaptan or the like in a solvent such as $CH_2Cl_2$, $Et_2O$, THF, $C_6H_6$, or the like at a temperature of from 0° to 25° C. for from 0.5 to 3 hours provides 8'. In the alternative 7' may be converted directly to 6, then to 7 and 8 (I). Conversion of either 8' or 7' to 6 is accomplished by treating either with $(R^3)_2$ CuLi or $(R^3)_2$CuMgX wherein $R^3$ is as defined above (the ultimate 2-substituent on species 8, otherwise known as (I) in a solvent such as diethylether, tetrahydrofuran, or the like at a temperature of from −78° to 25° C. for from 10 min. to 2 hours. It will be recognized that species 6 (above) is identical to species 6 in the first-defined total reaction scheme and that conversion of 6→7→8 (I) is exactly as described above.

In the generic description of the present invention (I, above), the substituents $R^1$, $R^2$, $R^3$ and $R^4$ are preferably selected from the group consisting of hydrogen ($R^4$ is not H); substituted and unsubstituted: straight and branched loweralkyl having from 1 to 10 carbon atoms; alkenyl, alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl furyl and the like; heterocyclylalkyl which comprises the immediately preceding heterocyclyl moieties and the alkyl moiety comprises from 1 to 10 carbon atoms; the substituent (or substituents) relative to the abovenamed radicals is selected from the group consisting of amino, hydroxyl, cyano, carboxyl, nitro, chloro, bromo, fluoro, lower alkoxy having from 1 to 6 carbon atoms, mercapto, perhaloloweralkyl such as trifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

A particularly preferred class of compounds are those wherein: $R^4$ is lower alkyl having from 1–6 carbon atoms such as methyl, ethyl, isopropyl and the like, phenyl or phenylalkyl having 7 to 10 carbon atoms; $R^1$, $R^2$, and $R^3$ are all hydrogen as well as those compounds wherein either $R^1$ or $R^2$ is hydrogen and $R^3$ is selected from the group consisting of substituted and unsubstituted: loweralkyl having from 1 to 6 carbon atoms, alkenyl having from 2 to 6 carbon atoms, and phenyl; $R^1$ is an α-substituted alkyl wherein the α-substituent is hydroxyl, amino or mercapto and wherein the alkyl moiety is straight or branched and comprises 1 to 6 carbon atoms; the substituents relative to the abovenamed preferred radicals are selected from the group consisting of hydroxyl, amino, amidino, guanidino, phenyl, mercapto, carboxyl, trifluoromethyl, loweralkylthio and loweralkoxyl wherein the alkyl moiety of the loweralkylthio and loweralkoxyl comprises 1 to 6 carbon atoms.

The preferred esters used as protecting groups are those where R′ is benzyl, p-nitrobenzyl, o-nitrobenzyl, t-butyl, bromo-t-butyl, t-butyl-dimethylsilyl, trimethylsilyl, trichloroethyl; or R′ represents pharmaceutically acceptable ester moieties such as pivaloyloxymethyl, allyl, methallyl, (2-methylthio)-ethyl, or 3-buten-1-yl.

Embodiments of structure I, above, wherein $R^4$ is H:

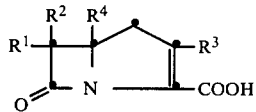

are disclosed and claimed in co-pending, commonly assigned U.S. Patent Application Ser. No. 843,171, non abandoned. This application is incorporated herein by reference, since the instantly described total synthesis is by analogy to the incorporated application. The instant process differs only in the $R^4$-substituted acyloxybutadiene starting material.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N′-dibenzylethylenediamine, diethanolamine, piperazine, dimethylaminoethanol, 2-amino-2-methyl-1-propanol, theophylline, N-methylglucamine and the like.

Salts of the amino group carried in certain species of I on side chains $R^1$, $R^2$, $R^3$ and $R^4$ are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unitdosage pharmaceutical forms. Also, they may be combined with other drugs to provide compositions having a board spectrum of activity.

The novel 1-carba-2-penem-3-carboxylic acids of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa,* Pseudomonas and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All reaction temperature are in °C.

EXAMPLE 1

Preparation of 1-carba-2-penem-5-methyl-3-carboxylic acid; and the benzyl ester and sodium salt thereof

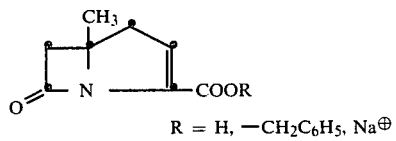

R = H, —CH$_2$C$_6$H$_5$, Na$^\oplus$

Step A: 1-(Benzyloxycarbonylhydroxymethyl-4-methyl)-4-(2-acetoxyethyl)-2-azetidinone

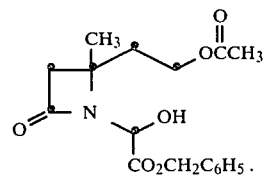

Dibenzyl tartarate, 2.0 g, is dissolved in 8 ml tetrahydrofuran (THF) and placed under N$_2$; periodic acid 1.7 g, dissolved in THF (80 ml) is added all at once and the reaction mixture is stirred vigorously for 30 minutes at 25° C. The resulting solution is filtered; the filtrate is evaporated; the residue is taken up in benzene (50 ml); filtered again; and finally evaporated to give benzylglyoxalate mixed with its hydrate. The 4-(2-acetoxyethyl)-4-methyl azetidinone, 1.0 g, is dissolved in benzene (80 ml) in a 3 neck flask fitted with a Dean-Stark water separator containing 2 g CaH$_2$ to trap the water, and a dropping funnel. The solution is refluxed until the CaH$_2$ shows no further reaction. The benzylglyoxalate and its hydrate from above is dissolved in benzene (80 ml) and added dropwise to the refluxing solution of the azetidinone over 1 hour; the reaction mixture is then refluxed another 3 hours. The reaction mixture is cooled and filtered. The filtrate is evaporated and the residue chromatographed on silica gel using 25% ethylacetate/benzene containing 1% methanol to give 1.85 g of product: 1-(benzyloxycarbonylhydroxymethyl)-4-(2-acetoxyethyl)-4-methyl-2-azetidinone.

Step B: 1-(Benzyloxycarbonylchloromethyl)-4-methyl-4-(2-acetoxyethyl)-2-azetidinone

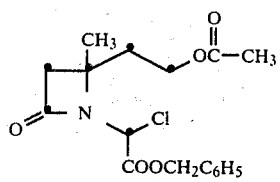

1-(Benzyloxycarbonyl hydroxymethyl)-4-(2-acetoxyethyl)-4-methyl-2-azetidinone (1.8 g) is dissolved in 30 ml THF under $N_2$ and cooled to $-20°$ C. Pyridine 0.45 ml is added and then thionylchloride (0.390 ml in 4 ml THF) is added dropwise over 2 minutes. The reaction mixture is stirred at $-20°$ C., for 5 minutes. The cooling bath is removed and the reaction mixture is stirred for another 25 minutes. The reaction mixture is diluted with 30 ml benzene and filtered. The filtrate is evaporated under reduced pressure at 5° C. The residue is 1-(benzyloxycarbonylchloromethyl)-4-(2-acetoxyethyl)-4-methyl-2-azetidinone which is used directly in the next reaction.

Step C: 1-(Benzyloxycarbonylmethylenetriphenylphosphoranyl)-4-(2-acetoxyethyl)-4-methyl-2-azetidinone

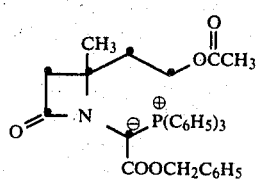

The 1-(benzyloxycarbonylchloromethyl)-4-(2-acetoxyethyl)-4-methyl-2-azetidinone (1.8 g) from Step B is dissolved in dimethylformamide (DMF) (20 ml) and treated with triphenylphosphine (1.47 g). The reaction mixture is stirred under $N_2$ at 25° C., for 1 hour. The DMF is removed under reduced pressure and the residue is taken up in $CH_2Cl_2$ and washed with pH 7 phosphate buffer. The $CH_2Cl_2$ solution is dried and evaporated to give the crude product. Chromatography on silica gel using ethylacetate as eluant gives 2.9 g 1-(benzyloxycarbonylmethylenetriphenylphosphoranyl)-4-(2-acetoxyethyl)-4-methyl-2-azetidinone.

Step D: 1-(Benzyloxycarbonylmethyltriphenylphosphoranyl)-4-(2-hydroxyethyl)-4-methyl-2-azetidinone

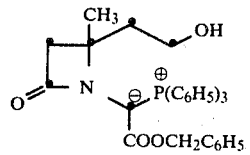

The 1-(benzyloxycarbonylmethylenetriphenylphosphoranyl)-4-(2-acetoxyethyl)-4-methyl-2-azetidinone (2.9 g) from Step C is dissolved in methanol (100 ml) and treated with 0.300 g of sodium methoxide. The reaction mixture is stirred under $N_2$ at 25° C., for 1 hour. Most of the methanol is removed under reduced pressure. The residue is taken up in 150 ml $CH_2Cl_2$ and washed once with pH 7 buffer, then dried and evaporated. The residue is chromatographed on silica gel using 5% methanol in ethylacetate as eluant to give 2.4 g of 1-(benzyloxycarbonylmethylenetriphenylphosphoranyl)-4-methyl-4-(2-hydroxyethyl)-2-azetidinone.

Step E: Benzyl-1-carba-2-penem-5-methyl-3-carboxylate

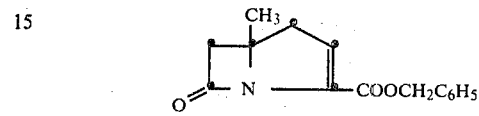

The 1-(benzyloxycarbonylmethylenetriphenylphosphoranyl)-4-methyl-4-(2-hydroxyethyl)-2-azetidinone (0.546 g) from Step D is dissolved in 10 ml dimethylsulfoxide (DMSO) and 10 ml of acetic anhydride is added. The reaction mixture is stirred under $N_2$ at 25° C., for 3.5 hours. The acetic anhydride and DMSO are removed under reduced pressure at 25° C., and the residue is purified by preparative thin layer chromatography on silica gel using 25% ethylacetate in benzene as eluant to give benzyl-1-carba-5-methyl-2-penem-3-carboxylate.

Step F: Sodium 1-carba-2-penem-5-methyl-3-carboxylate

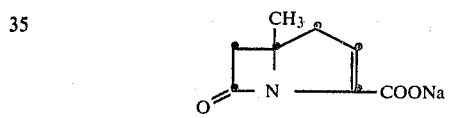

The Benzyl 1-carba-2-penem-5-methyl-3-carboxylate (0.010 g) from Step E is dissolved in 1 ml dioxane, treated with 1 ml $H_2O$ and 0.01 ml pH 7 0.5 molar phosphate buffer; 0.002 g of 10% Pd/C catalyst is added and the reaction mixture is reduced under $H_2$ at 40 lbs for 7 minutes. The catalyst is filtered off and washed with water. The filtrate and washings are extracted with $CH_2Cl_2$ and the aqueous phase is concentrated and freeze dried to give sodium 1-carba-2-penem-5-methyl-3-carboxylate.

EXAMPLE 1a

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml. DMF and treated with o-nitrobenzyl chloride (20 g, 0.117 mole) and sodium iodide (17.5 g, 0.117 mole). The mixture is stirred under $N_2$ for 2½ days at 65° C.

The solvent is removed under vacuum and the resulting paste is treated with water and sodium thiosulfate (5 g). The resulting solid is filtered and dried to give di-o- nitrobenzyltartarate (17.0 g, 0.040 mole, 69%, m.p. 128° C.).

n.m.r. (DMSO) δ: 4.8 d (j=7, H—C—OH), 5.23 d (j=7, H—C—OH), 5.7 S (O—CH₂—C₆H₄—NO₂); 7.73 & 8.2 m (aromatic H).

Similar treatment of the di-lithium salt with R′X (where X=Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate. These can be used as alternates to di-benzyl tartarate in Example 1.

EXAMPLE 2

Preparation of Sodium 6α-(1-hydroxyethyl)-1-carba-2-penem-5-methyl-3-carboxylate

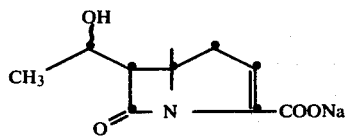

Step A: Benzyl 6α-(1-methylthiomethyleneoxy)ethyl-2-penem-3-carboxylate

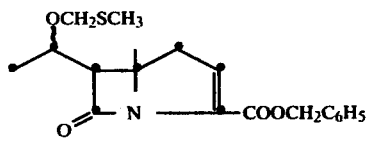

Following exactly the procedures described for conversion of 4-(2-acetoxyethyl)-4-methyl-azetidinone to benzyl-1-carba-2-penem-5-methyl-3-carboxylate, there is obtained benzyl-6α-(1-methylthiomethyleneoxy)ethyl-1-carba-2-penem-5-methyl-3-carboxylate from trans-3-(1-methylthiomethyleneoxy)-ethyl-4-(2-acetoxyethyl)-4-methyl-2-azetidinone.

Step B: Benzyl 6α-(1-hydroxyethyl)-1-carba-5-methyl-pen-2-em-3-carboxylate

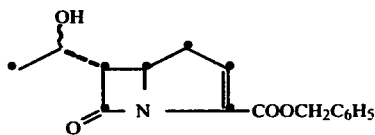

Benzyl 6α-(1-methylthiomethyleneoxy)-ethyl-2-penem-5-methyl-3-carboxylate (0.100 g) is dissolved in 4 ml acetonitrile 1 ml water. Mercuric chloride 1.5 eq is added and the mixture is stirred at 25° C. for 4 hrs. The reaction mixture is filtered through celite and washed with EtOAc. The filtrate and washings are washed with a solution of ammonium chloride then dried and evaporated. The residue is purified by preparative t.l.c. silica gel to give Benzyl-6α-(1-hydroxyethyl)-2-penem-5-methyl-3-carboxylate.

Step C: Sodium 6α-(1-hydroxyethyl)-1-carba-5-methyl-2-penem-3-carboxylate

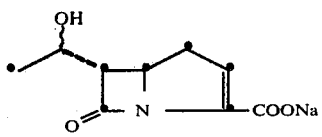

Benzyl 6α-(1-hydroxyethyl)-5-methyl-3-carboxylate is hydrogenated using the procedure described in Step F, Example 1 to give sodium 6α-(1-hydroxyethyl)-2-penem-5-methyl-3-carboxylate.

EXAMPLE 3

Preparation of trans-3-(1-methylthiomethyleneoxy)-ethyl-4-methyl-4-(2-acetoxyethyl)-2-azetidinone

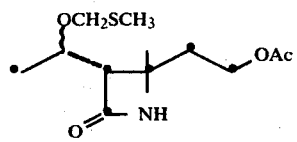

Step A: 8-oxo-2,2,6-trimethyl-7α-(1-hydroxyethyl)-3-oxa-1-azabicyclo[4.2.0]octane

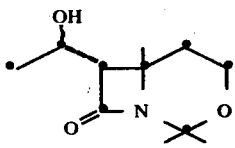

Tetrahydrofuran (THF), 20 ml is placed under N₂, treated with 1.54 ml diisopropylamine and cooled to −78° C. A solution of n-butyl lithium 1.97 M in hexane 5.6 ml is added dropwise over 5 min. The reaction mixture is stirred at −78° C. for 10 min and then treated with 8-oxo-2,2,6-trimethyl-3-oxa-1-azabicyclo[4.2.0]octane 1.55 g in 15 ml THF added dropwise over 5 min. After another 10 min hexamethylphosphoramide 1.97 ml is added. The resulting mixture, containing the lithium enolate of 8-oxo-3-oxa-2,2,6-trimethyl-azabicyclo[4.2.0]octane, at −78° is stirred another 10 min, then treated with an excess of acetaldehyde. The reaction mixture is stirred at −78° C. for 15 min and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C₆H₆ as eluant to give 8-oxo-2,2,6-trimethyl-7α-(1-hydroxyethyl)-3-oxa-1-azabicyclo[4.2.0]octane.

Step b: 8-oxo-7α-(1-methylthiomethyleneoxy)-ethyl-3-oxa-1-azabicyclo[4.2.0]octane

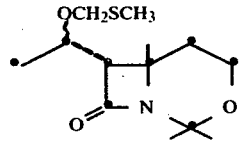

8-oxo-3-oxa-2,2,6-trimethyl-7α-(1-hydroxyethyl)-1-azabicyclo[4.2.0]Octaine (1.04 g) is dissolved in 5 ml DMF under N₂ and treated with sodium hydride (0.330 g 57% in mineral oil, 1.5 eq). The reaction mixture is stirred for 1 hour. Chloromethylsulfide (0.964 ml, 2-eq)

is added and the reaction mixture is stirred another 2 hours. Acetic acid (0.5 ml) is added to destroy excess sodium hydride and the reaction mixture is evaporated to dryness under reduced pressure below 40° C. The residue is taken up in CH₂Cl₂, washed with water, dried and evaporated. The residue is chromatographed to give 8-oxo-2,2,6-trimethyl-7α-(1-methylthiomethyleneoxy)-ethyl-3-oxa-1-azabicyclo[4.2.0]octane.

Step C: Trans-3-(1-methylthiomethyleneoxy)ethyl-4-(2-hydroxyethyl)-4-methyl-2-azetidinone

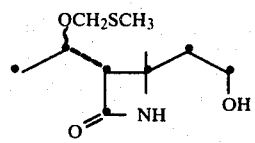

8-oxo-3-oxa-2,2,6-trimethyl-7α-(1-methylthiomethyleneoxy)-ethyl-1-azabicyclo[4.2.0]octane (0.460 g) is dissolved in 8 ml acetic acid and 2 ml H₂O and allowed to stand at 25° C. for 48 hrs. The acetic acid and H₂O are removed under reduced pressure. The residue is purified by preparative t.l.c. to give trans-3-(1-methylthiomethyleneoxy)ethyl-4-(2-hydroxyethyl)-4-methyl-2-azetidinone.

Step D: Trans-3-(1-methylthiomethyleneoxy)ethyl-4-methyl-4-(2-acetoxyethyl)-2-azetidinone

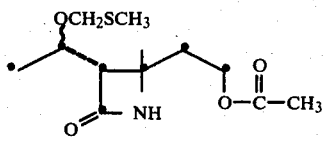

Trans-3-(1-methylthiomethyleneoxy)ethyl-4-(2-hydroxyethyl)-4-methyl-2-azetidinone is dissolved in 10 ml CH₂Cl₂ and cooled to 0°. Pyridine (0.75 ml) is added and then 0.392 ml of acetyl chloride is added dropwise. The mixture is stirred at 0° for 15 minutes, then at 25° for another 15 minutes, and then evaporated to dryness. The residue is chromatographed on silica gel using 50% EtOAc/C₆H₆ as eluant to give trans-3-(1-methylthiomethyleneoxy)ethyl-4-methyl-4-(2-acetoxyethyl)-2-azetidinone.

EXAMPLE 4

Preparation of 4-methyl-4-(2-Acetoxyethyl)-Azetidinone, 3-(1-hydroxyethyl)-4-(2-acetoxyethyl)-4-methyl-Azetidinone, and 3-(1-hydroxyethyl)-4-(2-hydroxyethyl)-4-methyl-Azetidinone Step A
Preparation of 4-methyl-4-(2-acetoxyvinyl)azetidine-2-one

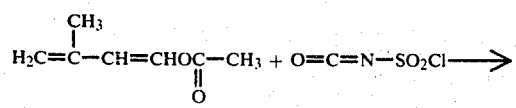

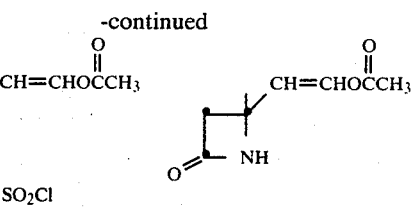

A solution of 1.0 ml distilled chlorosulfonylisocyanate (1.65 g; 11.7 mmoles) in 2.5 ml anhydrous diethyl ether is cooled under N₂ in a −20° C. bath.

A solution of 2.5 g 1-acetoxy-3-methyl-butadiene in 2.5 ml anhydrous ether is similarly cooled under N₂ in a −20° C. bath.

The chlorosulfonylisocyanate solution is added dropwise to the acetoxy-3-methyl-butadiene solution by means of a Teflon tube immersed in the CSI solution and pressurized with N₂. The addition takes 10 minutes. The reaction is stirred at −20° C. for 0.5 hour.

A solution of 2 g sodium sulfite and 5 g K₂HPO₄ in 20 ml H₂O is prepared during the above 0.5 hour reaction time and is cooled in an ice bath; 20 ml of ether is added and the mixture is vigorously stirred in an ice bath. At the end of the 30 minute reaction time, the reaction mixture is transferred, again using N₂ pressure and the Teflon tube, from the reaction flask which is maintained in the −20° C. bath to the vigorously stirred hydrolysis mixture. Rapid dropwise addition is completed in 5 minutes. The hydrolysis is allowed to cintinue for 5 additional minutes. The hydrolysis mix has a pH of 6–8, preferably pH 8.

The phases are separated. The ether phase is dried directly with MgSO₄. The aqueous phase is extracted three more times with 50 ml portions of ether, each being added to the initial ether/MgSO₄.

The dried extracts are filtered and concentrated and the residue chromatographed to give the product.

Step B:
Preparation of 4-methyl-4-(2-Acetoxyethyl)-2-Azetidinone

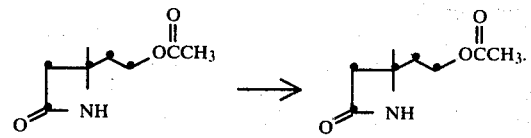

A solution of 4-methyl-4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-methyl-4-(2-acetoxyethyl)-2-azetidinone.

Step C:
Preparation of 4-Methyl-4-(2-hydroxyethyl)-2-azetidinone

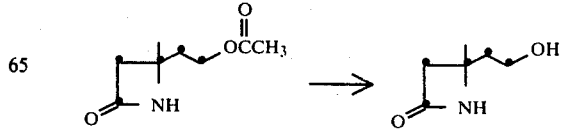

Under nitrogen at 0°, a solution of 4-methyl-4-(2-acetoxyethyl)-2-azetidinone (2.24 g) in 25 ml anhydrous methanol is treated with a solution of sodium methoxide (77 mg) in 5 ml anhydrous methanol. After stirring for 1 hour, the solution is neutralized with glacial acetic acid. Removal of the methanol in vacuo gives crude 4-methyl-4-(2-hydroxyethyl)-2-azetidinone. The product is purified by chromatography on silica gel to give the product.

Step D:
Preparation of 8-Oxo-2,2,6-trimethyl-3-oxa-1-azabicyclo-[4.2.0]octane

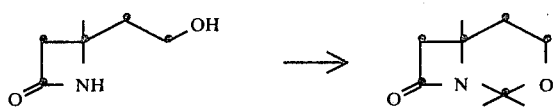

A solution of 4-methyl-4-(2-hydroxyethyl)-2-azetidinone (0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. After removal of the solvent under reduced pressure, chromatography of the crude product on silica gel gives 8-oxo-2,2,6-trimethyl-3-oxa-1-azabicyclo[4.2.0]octane.

Step E:
Preparation of 8-oxo-2,2,6-trimethyl-7α and β-(1-hydroxyethyl)-3-oxa-1-azabicyclo/4.2.0/octane

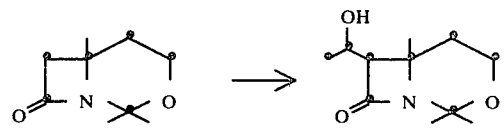

To a solution of 1.1 equivalents of freshly prepared lithium diisopropylamide in anhydrous tetrahydrofuran under a nitrogen atmosphere at −78° is added a solution of 8-oxo-2,2,6-trimethyl-3-oxa-1-azabicyclo[4.2.0]-octane in anhydrous tetrahydrofuran which has been cooled to −78° C. After two minutes, the resulting lithium enolate is treated with excess acetaldehyde. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2,6-trimethyl-7α and β-(1-hydroxyethyl)-3-oxa-1-azabicyclo-[4.2.0]octane.

Step F:
Preparation of 8-Oxo-2,2,6-trimethyl-7α-(1-p-nitrobenzyl-carbonyldioxyethyl)-3-oxa-1-azabicyclo[4.2.-0]octane

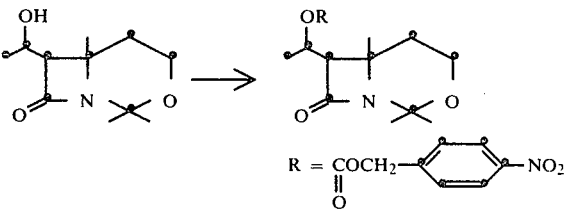

Under anhydrous conditions at 0° C. a solution of 8-oxo-2,2,6-trimethyl-7α-(1-hydroxyethyl)-3-oxa-1-azabicyclo[4.2.0]octane (60 mg,) in 0.6 ml ether is treated with powdered potassium hydroxide (19 mg). After a period of 15 minutes, p-nitrobenzyl chloroformate (65 mg,) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure and purification by preparative thick-layer chromatography on silica gel gives 8-oxo-2,2,6-trimethyl-7α-(1-p-nitrobenzylcarbonyldioxyethyl)-3-oxa-1-azabicyclo[4.2.0]octane as a mixture of diastereoisomers. The 7β-diastereoisomers or the 7α and β-mixture are obtained in an analogous manner.

Step G:
Preparation of Cis and Trans-3-(1-p-nitrobenzyloxycarbonyl-oxyethyl)-4-methyl-4-(2-hydroxyethyl)-2-azetidinone

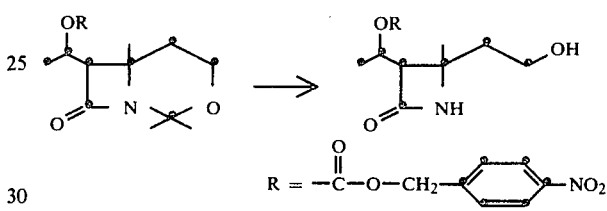

8-Oxo-3-oxa-2,2,6-trimethyl-7α-(1-p-nitrobenzyloxycarbonyloxyethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give trans-3-(1-p-nitrobenzyloxycarbonyloxyethyl)-4-methyl-4-(2-hydroxyethyl)-2-azetidinone as a mixture of diastereoisomers.

The cis diastereoisomers or the cis-trans mixture are obtained in an analogous manner.

Hydrogenation of 3-(1-p-nitrobenzyloxycarbonyloxyethyl)-4-methyl-4-(2-hydroxyethyl)-2-azetidinone according to the procedure of Example 1 Step F provides 3-(1-hydroxyethyl)-4-methyl-4-(2-hydroxyethyl)-2-azetidinone, which upon acetylation provides 3-(1-hydroxyethyl)-4-methyl-4-(2-acetoxyethyl)-2-azetidinone.

EXAMPLE 5

Preparation of 1-(t-butyldimethylsilyl)-4-methyl-4-(2-acetoxyethyl)-2-azetidinone

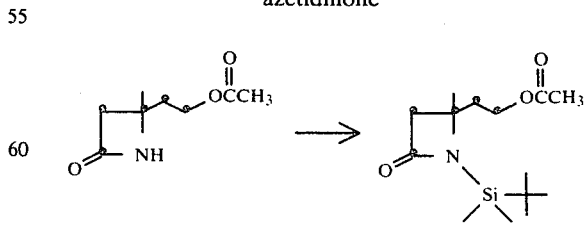

A solution of 4-methyl-4-(2'-acetoxyethyl)-2-azetidinone (50.2 g) and t-butyldimethylchlorosilane (50.6 g) in 250 ml anhydrous N,N-dimethylformamide is treated at 0° with triethylamine (35.6 g). The mixture is stirred for a period of five minutes. It is then partitioned between 1600 ml benzene and 600 ml water. The organic phase is washed an additional four times with water and finally with brine. The benzene solution is then dried over magnesium sulfate and filtered. Evaporation of the filtrate under reduced pressure gives 1-(t-butyldimethylsilyl)-4-methyl-4-(2'-acetoxyethyl)-2-azetidinone.

EXAMPLE 6

1-(t-butyldimethylsilyl)-4-methyl-4-(2-hydroxyethyl)-2-azetidinone

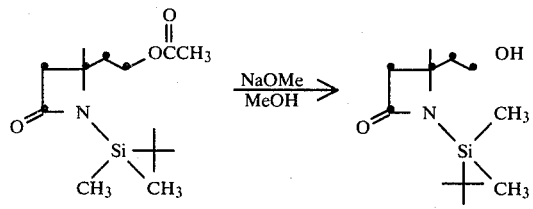

1-(t-butyldimethylsilyl)-4-methyl-4-(2-acetoxyethyl)-2-azetidinone (1.94 g, 7.15 mmol) is dissolved in anhydrous methanol (20 ml) cooled to 0° and a solution of NaOMe (0.36 mmol) in MeOH (0.5 ml) is added to the mixture stirred at 0° for 2 hours. HOAC (0.1 ml) is added the mixture is evaporated under vacuum and the residue is taken up in $CH_2Cl_2$; washed with water, 5% $NaHCO_3$, dried and evaporated to a pale yellow oil This is chromatographed on silica gel using EtOAc as eluant, to give 1-(t-butyldimethylsilyl)-4-methyl-4-(2-hydroxyethyl)-2-azetidinone.

EXAMPLE 7

1-(t-butyldimethylsilyl)-4-methyl-4-(2-oxoethyl)-2-azetidinone

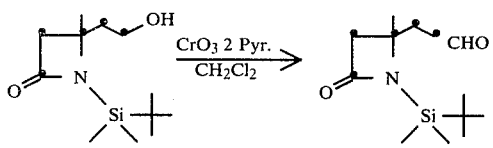

Anhydrous $CrO_3$ (1.94 g, 19.38 mmol) is added to a solution of anhydrous pyridine (3.07 g, 38.76 mmol) in anhydrous $CH_2Cl_2$ (50 ml). The resulting mixture is stirred at r.t.(22° C.) for 15 min. A solution of 1-(t-butyldimethylsilyl)-4-methyl-4-(2-hydroxyethyl)-2-azetidinone (0.74 g) in anhydrous $CH_2Cl_2$ 5 ml is added all at once. After stirring for 5 min, the $CH_2Cl_2$ solution is separated from a dark gummy precipitate which is washed with more $CH_2Cl_2$. The combined $CH_2Cl_2$ solution is evaporated under vacuum. The residue is taken up in ether filtered and washed with 5% $NaHCO_3$, 5% HCl, 5%$NaHCO_3$ and brine then dried and evaporated to give the aldehyde.

EXAMPLE 8

1-(t-butyldimethylsilyl)-4-methyl-4-(2-hyroxypropyl)-2-azetidinone

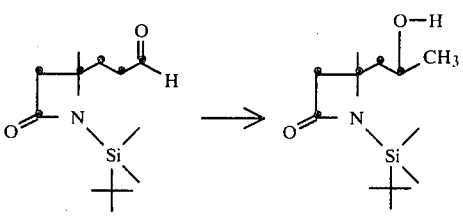

1-(t-butyldimethylsilyl)-4-methyl-4-(2-oxoethyl)-2-azetidinone (2.27 g, 0.01 mole) is dissolved in 50 ml ether and cooled to −20° C. under $N_2$. A solution of $CH_3MgBr$ in ether (0.011 mole $CH_3MgBr$) is added dropwise over ½ hours at −20° C. and the reaction mixture is stirred for another ½ hr at −20°, allowing to rise to 25° C. The reaction mixture is treated with a saturated solution of $MgSO_4$ (2 ml) and allowed to stir for 15 min. The Mg salts are filtered off and washed with ether. The combined filtrate and washings are dried and evaporated. Chromatography of the residue on silica gel gives 1-(t-butyldimethylsilyl)-4-methyl-4-(2-hydroxypropyl)-2-azetidinone.

EXAMPLE 9

1-(t-butyldimethylsilyl)-4-methyl-4-(2-acetoxypropyl)-2-azetidinone

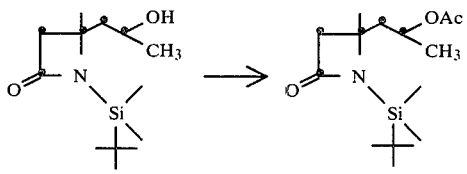

1-(t-butyldimethylsilyl)-4-methyl-4-(2-hydroxypropyl)-2-azetidinone (2.46 g) is dissolved in 20 ml $CH_2Cl_2$ cooled to 0° and treated with 0.90 g pyridine and 0.080 g of acetyl chloride (added dropwise). The reaction mixture is stirred at 0° for 15 min, allowed to warm to r.t. during the next 15 min and then worked up by dilution with $CH_2Cl_2$ and washing with water, drying and evaporating. The residue on chromatography on silica gel gives 1-(t-butyldimethylsilyl)-4-methyl-4-(2-acetoxypropyl)-2-azetidinone.

EXAMPLE 10

4-Methyl-4-(2-acetoxypropyl)-2-azetidinone

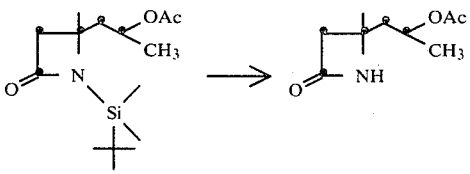

1-(t-butyldimethylsilyl)-4-methyl-4-(2-acetoxypropyl)-2-azetidinone (2.4 g) is dissolved in a solution of HCl in MeOH (0.25 N, 10 ml) and allowed to stand 2.5 hours at room temperature. The solvent is evaporated under reduced pressure and the residue is chromatographed on silica gel to give 4-methyl-4-(2-acetoxypropyl)-2-azetidinone.

EXAMPLE 11

Preparation of 4-methyl-4-(2-acetoxy-2-p-methoxyphenyl)-ethyl-2-azetidinone

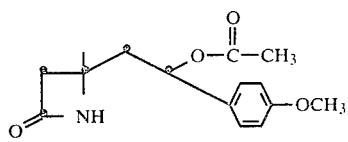

Treatment of 1-(t-butyldimethylsilyl)-4-methyl-4-(2-oxoethyl)-2-azetidinone (0.01 mole) with p-methoxyphenyl-magnesium bromide (1.1 eq.) in ether at 0° C. gives 2-azetidinone with p-methoxyphenyl-magnesium bromide gives 1-(t-butyl dimethylsilyl)-4-methyl-4-(2-hydroxyethyl-2-p-methoxyphenyl)-2-azetidinone which is acetylated to give 4-methyl-4-(2-acetoxy-2-p-methoxyphenyl)-2-azetidinone.

EXAMPLE 12

Preparation of 1-(t-butyldimethylsilyl)-3-acetyl-4-methyl-4-(2'-hydroxyethyl)-2-azetidinone

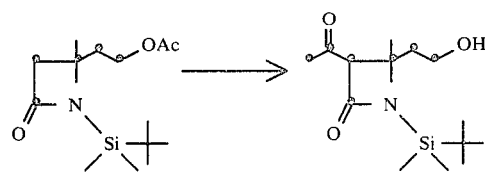

To a solution of 1.1 equivalents of freshly prepared lithium diisopropylamide in 3 ml anhydrous tetrahydrofuran under a nitrogen atmosphere at −78° is added a solution of 1-(t-butyldimethylsilyl)-4-methyl-4-(2'-acetoxyethyl)-2-azetidinone (61 mg, 0.225 mmole) in 1 ml anhydrous tetrahydrofuran which has been cooled to −78°. After 12 minutes the reaction mixture is poured into 5 ml water. The solution is saturated with sodium chloride and extracted with methylene chloride. The combined methylene chloride solutions are washed with brine, dried over magnesium sulfate and filtered. Evaporation of the filtrate under reduced pressure gives 50 mg of crude product. Purification by preparative thick-layer chromatography on silica gel developing with ethyl acetate gives 1-(t-butyldimethylsilyl)-3-acetyl-4-methyl-4-(2'-hydroxyethyl)-2-azetidinone.

EXAMPLE 13

Sodium 1-carba-2,2,5-dimethyl-2-penem-3-carboxylate

Step A 1-(o-nitrobenzyloxycarbonylmethyltriphenyl-phosphoranyl)-4-methyl-4-(carboxylmethyl)-2-azetidinone

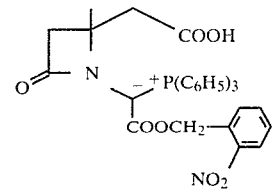

One gram of 1-(o-nitrobenzyloxycarbonylmethyltriphenylphosphoranyl)-4-methyl-4-(2-hydroxyethyl)-2-azetidinone is dissolved in 20 ml. acetone and cooled to 0° C. Jones Reagent (1 ml., 4 N solution) is added dropwise over 5 min and the resulting solution is stirred at 0° C. for 10 min. Isopropanol (0.1 ml) is added. The mixture is stirred for another 2 min. The reaction mixture is diluted with CH$_2$Cl$_2$ and filtered. The filtrate is washed with saturated NaCl solution, dried and evaporated to give 0.851 g of crude acid which is used without further purification in the next step.

Step B 1-(o-nitrobenzyloxycarbonylmethyltriphenylphosphoranyl)-4-methyl-4-(chlorocarbonylmethyl)-2-azetidinone

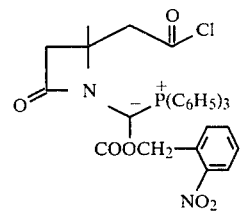

From Step A, 1-(o-nitrobenzyloxycarbonylmethyltriphenylphosphoranyl)-4-methyl-4-(carboxymethyl)-2-azetidinone (0.851 g) is dissolved in 20 ml CH$_2$Cl$_2$ and cooled to 0° C. under N$_2$. Oxalyl chloride (0.8 ml) is added dropwise over 5 min and then 1 drop of DMF is added. The mixture is stirred at 0° C. for 5 min and then at 25° C. for 15 min. The solvent and excess oxalyl chloride are evaporated under reduced pressure. The residue is the desired acid chloride which is used without purification in the next step.

Step C 1-(o-nitrobenzyloxycarbonyl triphenylphosphoranylmethyl) 4-methyl-4-(phenylthiocarbonylmethyl)-2-azetidinone

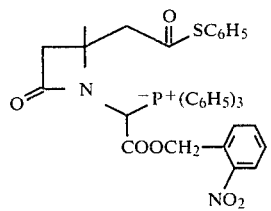

The product from Step B is dissolved in 20 ml CH$_2$Cl$_2$ and cooled to 0°, under N$_2$. Thiophenol (0.4 g) is added and then pyridine 0.8 ml is added dropwise. The reaction mixture is stirred at 0° for 5 min, then at 25° C. for 15 min, then diluted with CH$_2$Cl$_2$ and washed with water, dried and evaporated. The residue is chromatographed on silica gel using 50% EtOAc/C$_6$H$_6$ as eluant, to give 0.780 g of the thio ester.

Step D
1-(o-nitrobenzyloxycarbonyl-triphenylphosphoranyl-methyl)-4-methyl-4-(methylcarbonylmethyl)-2-azetidinone

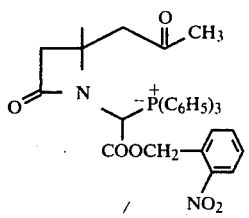

Cuprous iodide (0.380 g) is suspended in 10 ml anhydrous ether under N₂, in a dry flask and cooled to −20°. Methyl lithium (3.0 ml, 1.3 Molar) is added dropwise and the mixture is stirred at −20° for 5 min. to give a yellow suspension. The mixture is then cooled to −50°. 1-(o-nitrobenzyloxycarbonyl-triphenylphosphoranyl-methyl)-4-(phenylthiocarbonylmethyl)-2-azetidinone (0.674 g) in 10 ml THF is added dropwise over 5 min. The mixture is stirred at −50° for 5 min and allowed to come to −20° over 20 min and stirred at −20° for 5 min. Saturated NH₄Cl solution 5 ml is added and the mixture is diluted with CH₂Cl₂. Stirred at r.t. for 5 min. The organic phase is separated, dried and evaporated. The residue is chromatographed on silica gel using EtOAc as eluant to give the product.

Step E
o-Nitrobenzyl-1-carba-2,5-dimethyl-2-penem-3-carboxylate

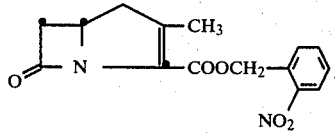

In xylene (3 ml) is dissolved 1-(o-nitrobenzyloxycarbonyltriphenylphosphoranylmethyl)-4-methyl-4-(methylcarbonylmethyl)-2-azetidinone (0.30 g), pyridine 0.010 ml is added and the mixture is heated under N₂ at 140° for 40 min. The xylene is removed under reduced pressure and the residue is purified by preparatory thin layer chromatography on silica gel using 50% EtOAc/C₆H₅ as eluant to give o-nitrobenzyl-1-carba-2,5-dimethyl-2-penem-3-carboxylate.

Step F
Sodium-1-carba-2,5-dimethyl-2-penem-3-carboxylate

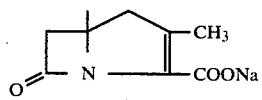

The product of Step E, o-nitrobenzyl-1-carba-2-methyl-2-penem-3-carboxylate, (0.010 g) is dissolved in dioxane (2 ml) and water (2 ml) pH 7 phosphate buffer (0.1 ml, 0.5 Molar) is added and the mixture is deoxygenated by bubbling N₂ through the mixture. The mixture is photolysed for 1 hr using 350 nm light in a pyrex vessel cooled by a cold finger. The photolysis mixture is extracted with ethyl acetate. The aqueous phase is freeze dried to give sodium-1-carba-2,5-dimethyl-2-penem-3-carboxylate.

EXAMPLES 14–15

Sodium 1-carba-2-phenyl-5-methyl-2-penem-3-carboxylate

Step A
1-(o-nitrobenzyloxycarbonyltriphenylphosphoranyl-methyl, 4-methyl-4-(phenylcarbonylmethyl)-2-azetidinone

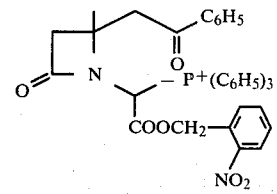

Following the procedure described in Example 39, Step D, but substituting an equivalent amount of phenyl lithium (or phenyl magnesium bromide) for methyl lithium, there is obtained 1-(o-nitrobenzyloxycarbonyl-triphenylphosphoranylmethyl)-4-methyl-4-(phenylcarbonylmethyl)-2-azetidinone.

Step B
o-nitrobenzyl-1-carba-2-phenyl-5-methyl-2-penem-3-carboxylate

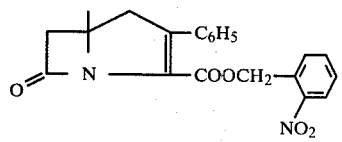

The product of Step A, 1-(o-nitrobenzyloxycarbonyltri-phenylphosphoranylmethyl)-4-(phenylcarbonylme-thyl)-2-azetidinone (0.030 g), is dissolved in xylene (3 ml) and heated under N₂, at 140° for 40 min. The xylene is removed under reduced pressure and the residue purified by preparatory tlc on silica gel to give o-nitro-benzyl-1-carba-2-phenyl-5-methyl-2-penem-3-carboxylate.

Step C
Sodium-1-carba-2-phenyl-5-methyl-2-penem-3-carboxylate

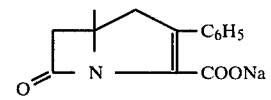

Photolysis of o-nitrobenzyl-1-carba-2-phenyl-2-penem-3-carboxylate by the procedure described in Example 39, Step F, gives sodium-1-carba-2-phenyl-2-penem-3-carboxylate. The same result is achieved by hydrogenolysis at 40 lbs, using dioxane, water as solvent, 1.0 equivalent of NaHCO₃ and 10% pd/c as catalyst.

EXAMPLE 16

Sodium 1-carba-2-(p-methoxyphenyl)-5-methyl-2-penem-3-carboxylate

Step A
1-(o-nitrobenzyloxycarbonyl-triphenylphosphoranyl-methyl-4-(p-methoxyphenylcarboxymethyl)-2-azetidinone

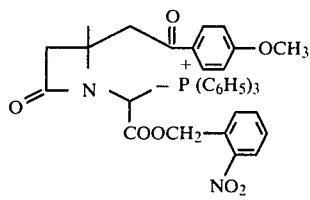

A solution of p-methoxybenzyl magnesium bromide (0.25 M in 50% Et₂O/THF, 0.8 ml, is placed under N₂ and cooled to 0°. Cuprous iodide (0.019 g) is added and the mixture is stirred at 0° for ½ hours; 1-(o-nitrobenzyloxycarbonyltriphenylphosphoranylmethyl)-4-methyl-4-(phenylthiocarbonylmethyl)-2-azetidinone (0.034 g) in 0.5 ml THF is added dropwise. The mixture is allowed to stir at 0° for 40 min. A saturated solution of NH₄Cl in H₂O is added and the mixture is allowed to stir for 15 min. The organic phase is separated. The aqueous phase is extracted twice with CH₂Cl₂. The combined organic extracted is dried, evaporated to give a residue which is separated by preparative tlc to give the product.

Step B
o-Nitrobenzyl-1-carba-2-(p-methoxyphenyl)-5-methyl-2-penem-3-carboxylate

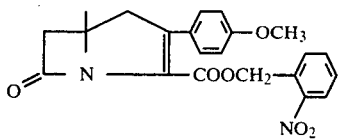

The product of Step A, 1-(o-nitrobenzyloxycarbonyl-triphenylphosphoranylmethyl)4-methyl-4-(p-methoxy-phenylcarbonylmethyl)-2-azetidinone (0.057 g), is dissolved in 5 ml xylene, placed under N₂ and heated at 140° for 3 hours. The xylene is removed under reduced pressure and the residue is purified by preparative tlc (50% EtOAc/C₆H₅ silica gel G) to give the product.

Step C
Sodium-1-carba-2-(p-methoxyphenyl)-5-methyl-2-penem-3-carboxylate

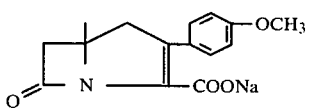

The product of Step B, o-nitrobenzyl-1-carba-2-(p-methoxyphenyl)-5-methyl-2-penem-3-carboxylate (10 mg), is dissolved in 5 ml dioxane, 1 ml EtOH and 5 ml H₂O; NaHCO₃ (2.2 mg, and 10 mg 10% Pd/C catalyst is added and the mixture is reduced under H₂ at 40 lbs for 45 minutes. The catalyst is filtered off and washed with 1 ml dioxane and 1 ml H₂O. The filtrate and washings are extracted with 3×10 ml EtOAc and then freeze dried to give sodium 1-carba-2-(p-methoxybenzyl)-5-methyl-pen-2-em-3-carboxylate.

EXAMPLE 17

Preparation of Sodium 1-carba-2-(p-methoxyphenyl)-5-methyl-6α-(1-(R)-hydroxyethyl)-2-penem-3-carboxylate

Step A
8-oxo-2,2,6-trimethyl-7α-(1-o-nitrobenzyloxycarbonyloxyethyl)-3-oxa-1-azabicyclo-[4.2.0]-octane

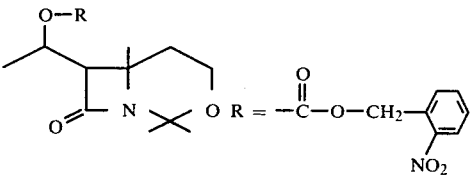

8-Oxo-2,2,6-trimethyl-7α-(1-hydroxyethyl)-3-oxa-1-aza-bicyclo-[4.2.0]-octane (3.0 g, 0.015 m) is dissolved in 40 ml THF and cooled to −78° under N₂. Methyl Lithium (13.3 ml, 1.3 m solution in Et₂O/C₆H₆) is added dropwise over 5 minutes and the mixture is stirred for 10 minutes; o-nitrobenzyloxycarbonylchloride (3.56 g, 0.0165 m) in 20 ml THF is added dropwise over 10 minutes and the mixture is stirred at −78° C. for 45 minutes. The mixture is treated with 20 ml of pH 7 phosphate buffer (0.5 m) and water. The organic phase is separated and the aqueous phase is extracted with CH₂Cl₂. The combined organic extract is dried and evaporated. The residue is chromatographed on silica gel using 50% EtOAc/cyclohexane to give 8-oxo-2,2,6-trimethyl-7α-(1-(R)-o-nitrobenzyloxycarbonyloxyethyl)-3-oxa-1-azabicyclo-[4.2.0]-octane and 8-oxo-2,2,6-trimethyl-7α-[1(S)-o-nitrobenzyloxycarbonyloxyethyl]-3-oxa-1-azabicyclo[4.2.0]octane.

Step B
trans-3-[1(R)-o-nitrobenzyloxycarbonyoxyethyl]-4-methyl-4-(2-hydroxyethyl)-2-azetidinone

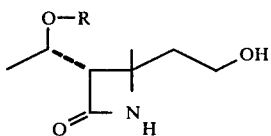

8-Oxo-2,2,6-trimethyl-7α-[1(R)-o-nitrobenzyloxycarbonyloxyethyl]-3-oxa-1-azabicyclo-[4.2.0]-octane (1.38 g) is dissolved in acetic acid (16 ml) and water (4 ml) is added and the mixture is heated at 65° for 1.5 hours. The solvent is removed under reduced pressure and the residue taken up in 10 ml xylene which is evaporated off under reduced pressure and this process is repeated twice. The residue is the crude trans-3[1(R)-o-nitrobenzyloxycarbonyloxyethyl]-4-methyl-4-(2-hydroxyethyl)-2-azetidinone, which is used in the next step without further purification.

Step C
trans 1-(o-nitrobenzyloxycarbonylhydroxymethyl)-3-[1(R)-o-nitrobenzyloxycarbonyoxyethyl]-4-methyl-4-(2-hydroxyethyl)-2-azetidinone

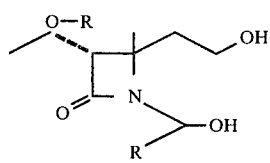

To trans-3[1(R)-o-nitrobenzyloxycarbonyloxyethyl]-4-methyl-4-(2-hydroxyethyl)-2-azetidinone from Step B in benzene (20 ml) is added o-nitrobenzylglyoxalate (prepared from 1.55 g di-o-nitrobenzyltartarate and 0.92 g periodic acid as described in Step A, Example 1 for benzylglyoxy. The mixture is refluxed overnight using a Dean-Stark apparatus with CaH₂ to trap the water. The mixture is cooled, filtered evaporated and chromatographed on silica gel using 70% EtOAC/C₆H₁₂ as eluant to give the diol.

Step D
trans 1-(o-nitrobenzyloxycarbonylhydroxymethyl)-3-[1(R)-o-nitrobenzyloxycarbonyloxyethyl]-4-methyl-4-(2-t-butyldimethylsilyloxy ethyl-2-azetidinone

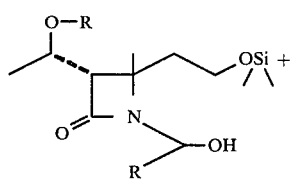

trans 1-(o-nitrobenzyloxycarbonylhydroxymethyl)-3-[1(R)-o-nitrobenzyloxycarbonyloxyethyl]-4-methyl-4-(2-hydroxyethyl)-2-azetidinone (0.825 g) is dissolved in 10 ml DMF and treated with t-butyldimethylchlorosilane (0.250 g) and triethylamine 0.233 g. The mixture is allowed to stir at r.t. for ½ hour. Water is added and the mixture is extracted with ether 3 times. The ether extract is washed with water 4 times, then dried evaporated and the residue chromatographed on silica gel using 50% EtOAc/C₆H₁₂ to give the silyl ether.

Step E
trans-1-(o-nitrobenzyloxycarbonyltriphenylphosphoranylmethyl)-3-[1(R)-o-nitrobenzyloxycarbonyloxyethyl]-4-methyl-4-(2-hydroxyethyl)-2-azetidinone

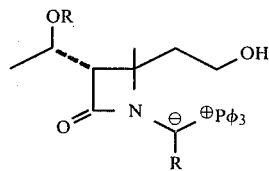

Trans 1-(o-nitrobenzyloxycarbonylhydroxymethyl)-3-[1(R)-o-nitrobenzyloxycarbonyloxyethyl]-4-methyl-4-(2-t-butyldimethylsilyloxy) ethyl-2-azetidinone (0.845 g) is treated with SOCl₂ (0.11 ml) and pyridine (0.13 ml) according to the procedure described in Example I Step B and the chloro compound so obtained is treated with triphenylphosphine (0.397 g) following the procedure of Example I Step C to give the DMF solution of the ylidsilylether. To this solution is added 0.1 ml concentrated HCl, the mixture is allowed to stir at 25° C. for 10 minutes. The solvent is removed under reduced pressure and the residue is taken up in CH₂Cl₂ and washed with 5% NaHCO₃ solution, dried evaporated and chromatographed on silica gel using 70% EtOAc/C₆H₁₂ to give trans-1-(o-nitrobenzyloxycarbonyltriphenylphosphoranylmethyl)-3-[1(R)-o-nitrobenzyloxycarbonylethyl]-4-methyl-4-(2-hydroxyethyl)-2-azetidinone.

Step F
trans-1-(o-nitrobenzyloxycarbonyltriphenylphosphoranylmethyl) 3-[1(R)-o-nitrobenzyloxycarbonyloxyethyl]-4-methyl-4-(carboxymethyl)-2-azetidinone

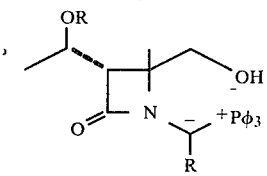

The product of Step E (0.700 g) is oxidized with Jones Reagent following the procedure of Step A Example 13 to give the carboxylic acid.

Step G
trans-1-(o-nitrobenzyloxycarbonyltriphenylphosphoranylmethyl)-3-[1(R)-o-nitrobenzyloxycarbonyloxyethyl]-4-methyl-4-(chlorocarbonylmethyl)-2-azetidinone

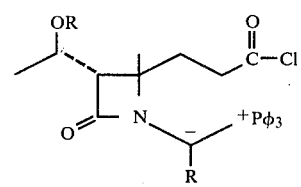

The product of Step F is treated with oxalyl chloride following the procedure of Step B Example 13 to give the acid chloride.

Step H
trans-1-(o-nitrobenzyloxycarbonyltriphenylphosphoranylmethyl)-3-[1(R)-o-nitrobenzyloxycarbonyloxyethyl]-4-methyl-4-[phenylthiocarbonylmethyl]-2-azetidinone

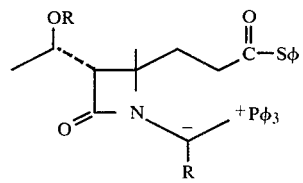

The product from Step G is treated with thiophenol and pyridine following the procedure described in Step C Example 13 to give the thioester.

Step I
trans-1-(o-nitrobenzyloxycarbonyltriphenylphosphoranylmethyl)-3-[1(R)-o-nitrobenzyloxycarbonyoxyethyl]-4-methyl-4-(p-methoxyphenylcarbonylmethyl)-2-azetidinone

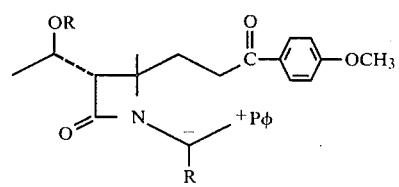

A solution (4 ml, 0.25 m) of p-methoxyphenyl magnesium bromide is placed in a dry flask under N₂ and cooled to −20°. Cu I (0.110 g) is added and the mixture is stirred under N₂ for 0.5 hour. The thioester from Step H (0.224 g) dissolved in THF (5 ml) is added dropwise followed by Et₂O (5 ml). The mixture is stirred at −20° for 45 minutes. Saturated NH₄Cl is added and the mixture is stirred open to air for 15 minutes. CH₂Cl₂ is added and the layers are separated. The aqueous layer is extracted once with CH₂Cl₂ and the total organic phase is dried and evaporated. Purification by preparative t.l.c. gives the ketone. In the foregoing steps B to I the word trans refers to the relative stereochemistry of 6-H and 5-CH₃.

Step J o-nitrobenzyl-1-carba-2-(p-methoxyphenyl)-5-methyl-6α-[1(R)-o-nitrobenzyloxycarbonyoxyethyl]-2-penem-3-carboxylate

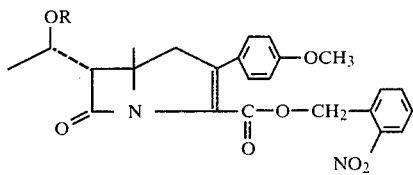

Trans-1-(o-nitrobenzyloxycarbonyltriphenylphosphoranylmethyl)-3-[1-(S)-o-nitrobenzyloxycarbonyloxyethyl]-4-methyl-4-(p-methoxyphenylcarbonylmethyl)-2-azetidinone (0.138 g) is dissolved in 6 ml xylene and heated under N₂ for 1 hour by an oil bath at 145°. The mixture is cooled, the solvent evaporated under reduced pressure and the residue purified by preparative t.l.c. to give the cyclized product and recovered starting material. This recovered ketone is heated in xylene as described above for another 3 hours to give after purification by preparative t.l.c. on silica gel 50% EtOAC/C₆H₁₂ eluant more of the cyclized product.

Step K

Sodium 1-carba-2-(p-methoxyphenyl)-5-methyl-6α-[1(S)hydroxyethyl]-2-penem-3-carboxylate

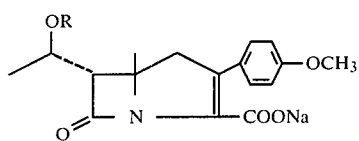

The product of Step J (0.020 g) is dissolved in 6 ml dioxane, 2.7 ml of a 1 mg/ml solution of NaHCO₃ is added followed by 3.3 ml of H₂O and 1.2 ml ETOH; Pd/C 10% (0.020 g) is added and the mixture is hydrogenated at 40 lbs. H₂ pressure for 1 hour. The catalyst is filtered off and washed with water. The filtrate and washings are extracted with 3×15 ml EtOAC and the aqueous phase is free-dried to give sodium 1-carba-2-(p-methoxyphenyl)-5-methyl-6α-[1(S)-hydroxyethyl]-2-penem-3-carboxylate.

EXAMPLE 17a

Following the procedures of the foregoing Examples and text, the following substituted azetidinone thioesters useful in the preparation of the compounds of the present invention are obtained.

TABLE I

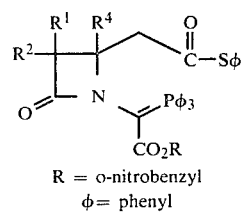

R = o-nitrobenzyl
φ = phenyl

| Compound | R₁ | R₂ | R⁴ |
|---|---|---|---|
| 1. | CH₃—C(R)(H)—O—C(=O)—O—CH₂—C₆H₄—NO₂ | H | CH₃ |
| 2. | CH₃—C(S)(H)—O—C(=O)—O—CH₂—C₆H₄—NO₂ | H | CH₃ |
| 3. | H | (CH₃)₂CH—O—C(=O)—O—CH₂—C₆H₄—NO₂ | CH₃ |
| 4. | CH₂=CH—CH₂—O—C(=O)—O—CH₂—C₆H₄—NO₂ | H | CH₃ |
| 5. | H | CH₂=CH—CH₂—O—C(=O)—OCH₂—C₆H₄—NO₂ | CH₃ |

TABLE I-continued

[Structure: R²—C(R¹)(—)—C(R⁴)(—)—CH₂—C(=O)—Sφ, with ring N—C(=O) and N—CH(Pφ₃)—CO₂R]

R = o-nitrobenzyl
φ = phenyl

| Compound | R₁ | R₂ | R⁴ |
|---|---|---|---|
| 6. | CH₃CH₂—CH(—O—C(=O)—O—CH₂—C₆H₄-NO₂) | H | CH₃ |
| 7. | CH₃—CH(—O—C(=O)—O—CH₂—C₆H₄-NO₂) | H | C₂H₅ |
| 8. | CH₃—CH(—O—C(=O)—O—CH₂—C₆H₄-NO₂) | H | C₆H₅ |
| 9. | CH₃—CH(—O—C(=O)—O—CH₂—C₆H₄-NO₂) | H | —CH(CH₃)₂ |
| 10. | CH₃—CH(—O—C(=O)—O—CH₂—C₆H₄-NO₂) | H | —CH₂—C₆H₅ |
| 11. | CF₃—CH(H)(—O—C(=O)—O—CH₂—C₆H₄-NO₂) | H | CH₃ |

1. As in Example 17, Steps A to H, starting with the (R) isomer of the product from Step A, Example 17.
2. As in Example 17, Steps A to H, starting with the (S) isomer of the product from Step A, Example 17.
3. As in Example 17, Steps A to H, starting with the β-product of Step E, Example 4.
4. As in Example 17, Steps A to H, but starting with the α-product of Step E, Example 4, wherein the aldol condensation is carried out using formaldhyde instead of acetatehyde.
5. As in Example 17, Steps A to H, but starting with the β-product of Step E, Example 4, wherein the aldol condensation is carried out using formaldehyde instead of acetatdehyde.
6. As in Example 17, Steps A to H, but starting with the α-product of Step E, Example 4, wherein the aldol condensation is carried out using propionaldehyde instead of acetatdehyde.
7. Starting with 1-acetoxy-3-ethyl-1,3-butadiene in Step A, Example 4, and using the product of Step E, Example 4 as starting material for Example 17, Steps A to H.
8. Starting with 1-acetoxy-3-phenyl-1,3-butadiene in Step A, Example 4, and using the product of Step E, Example 4 as starting material for Example 17, Steps A to H.
9. Starting with 1-acetoxy-3-isopropyl-1,3-butadiene in Step A, Example 4, and using the product of Step E, Example 4, as starting material for Example 17, Steps A to H.
10. Starting with 1-acetoxy-3-benzyl-1,3-butadiene in Step A, Example 4, and using the product of Step E, Example 4, as starting material for Example 17, Steps A to H.
11. As in Example 17, Steps A to H, but starting with the α-product of Step E, Example 4, wherein the aldol condensation is carried out using trifluoroacetatdehyde.

EXAMPLE 18

Following the procedures developed in the foregoing Examples and test, the following compounds of the present invention, I, are obtained. Remarks relative to the procedures are presented in the footnote to Table II.

TABLE II

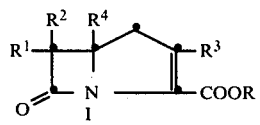

| Compound | R¹ | R² | R³ | R⁴ | R |
|---|---|---|---|---|---|
| 1 | H | H | H | CH₃ | Na |

TABLE II-continued

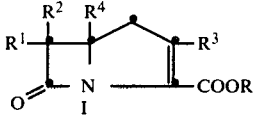

| Compound | R¹ | R² | R³ | R⁴ | R |
|---|---|---|---|---|---|
| 2 | CH₃-CH(OH)- | H | H | CH₃ | Na |
| 3 | HO—CH₂— | H | H | CH₃ | Na |
| 4 | H | H | CH₃ | CH₃ | Na |
| 5 | CH₃-CH(OH)- | H | CH₃ | CH₃ | Na |
| 6 | CH₃-CH(OH)- | H | CH₂—CH₂—OH | CH₃ | Na |
| 7 | CF₃-CH(OH)- | H | CH₃ | Na | |
| 8 | CH₃-CH(OH)- | H | CH₂—CH₂—NH₂ | CH₃ | Na |
| 9 | CH₃-CH(OH)- | H | CH—CH₂—NH—C(=NH)H | CH₃ | H |
| 10 | CH₃-CH(OH)- | H | —CH₂—CH₂—CH₂—NH—C(=NH)CH₃ | CH₃ | H |
| 11 | CH₃—CH₂—CH(OH)- | H | —CH₂—CH₂—NH—CHO | CH₃ | H |
| 12 | H | H | C₆H₅ | CH₃ | Na |
| 13 | H | H | —C₆H₄—OCH₃ | CH₃ | Na |
| 14 | CH₃-C(CH₃)OH | H | —C₆H₄—OCH₃ | CH₃ | Na |
| 15 | CH₃-C(CH₃)OH | H | —C₆H₄—CH₂OH | CH₃ | Na |
| 16 | CH₃-C(CH₃)OH | H | —C₆H₄—CH₂NH₂ | CH₃ | H |
| 17 | CH₃-C(CH₃)OH | H | —C₆H₄—COONa | CH₃ | H |
| 18 | CH₃-C(CH₃)OH | H | —C₆H₄—CH₂NH₂ | C₂H₅ | H |
| 19 | CH₃-C(CH₃)OH | H | —C₆H₄—CH₂OH | C₆H₅ | H |
| 20 | CH₃-C(CH₃)OH | H | —C₆H₄—CH₂NH₂ | | H |
| 21 | CH₃-C(CH₃)OH | H | —C₆H₄—CH₂NH₂ | CH₂C₆H₅ | H |
| 22 | CF₃-C(CH₃)OH | H | —C₆H₄—CH₂NH₂ | CH₃ | H |
| 23 | —CH₂—OH | H | —C₆H₄—CH₂NH₂ | CH₃ | H |

TABLE II-continued

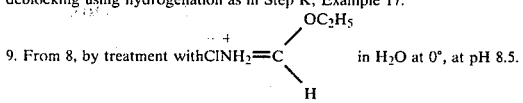

| Compound | R¹ | R² | R³ | R⁴ | R |
|---|---|---|---|---|---|
| 24 | CH₃—CH₂—C(OH)(\\) | H | 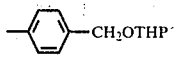—CH₂NH₂ | CH₃ | H |

1. Starting with the product of Step B, Example 4, and as shown in Example 1.
2. By oxidation of the product from Step E, Example 17, using DMSO and AC₂O and photolytic deblocking of the product as in Step F of Example 13.
3. Starting with the product of Step D, Example 4, and carrying out the aldol reaction as in Step E, Example 4, but using formaldehyde instead of acetaldehyde and reacting the aldol product as in Example 17, Steps A through E, and then as for 2 above.
4. As in Example 13.
5. Starting with the product of Step E, Example 17 and following the procedures of Example 13.
6. As in 5, except that the BrMgCH₂CH₂—OTHP is used instead of MeLi in the procedure of Step D, Example 13, and the THP ether is hydrolysed using 10% aq. E₂SO₄ in HOAc before proceeding on to the procedure of Step E, Example 13.
7. As in 3, except that the aldol reaction is carried out using CF₃CHO.
8. Starting with the product of hydrolysis of the THP ether described in 6 above and converting it into a mesylate and displacing with LiN₃ in DMF and then taking the azide through the Steps E, Example 13 and deblocking using hydrogenation as in Step K, Example 17.
9. From 8, by treatment with ClNH₂=C(OC₂H₅)(H)⁺ in H₂O at 0°, at pH 8.5.
10. As described for 8, but using Br-Mg-CH₂CH₂—CH₂—OTHP as the reagent.
11. As described for 9 except propionaldehyde is used in the aldol condensation of the product of Step D, Example 4.
12. As in Example 14–15.
13. As in Example 16.
14. As in Example 17.
15. As in Example 17, using

—⟨⟩—CH₂OTHP as the Grignard reagent in Step I and hydrolysing the THP ether with 10% aq. H₂SO₄/HOAc and following the procedures of Steps J and K. (HOAc = acetic acid.)
16. As for 15, but making the mesylate of the product of hydrolysis of the THP ether followed by displacement with LiN₃ in DMF, and then following the procedures of Steps J and K of Example 17.
17. As for 15, but oxidizing the product of hydrolysis of the THP either with Jones reagent, protecting the acid as the p-nitrobenzyl ester and following the procedures of Steps J and K of Example 17.
18. As for 16, but using the compound 7 of Table I as starting material for Step I, Example 17.
19. As for 15, but using the compound 8, of Table I as starting material for Step I, Example 17.
20. As for 16, but using the compound 9 of Table I as starting material for Step I, Example 17.
21. As for 16, but using the compound 10 of Table I as starting material for Step I, Example 17.
22. As for 16, but using the compound 11 of Table I as starting material for Step I, Example 17.
23. As for 16, but using the compound 4 of Table I as starting material for Step I, Example 17.
24. As for 16, but using the compound 6 of Table I as starting material for Step I, Example 17.

EXAMPLE 19

Preparation of Pharmaceutical Compositions

One such unit dosage form consists in mixing 120 mg. of 1-carba-2-(p-aminomethylphenyl)-6-(1'-hydroxyethyl)-5-methyl-pen-2-em-3-carboxylic acid (I) with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

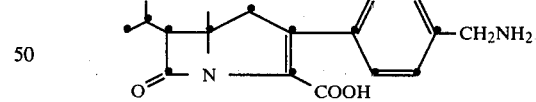

| TABLET | PER TABLET |
|---|---|
| 1-carba-2-(p-aminomethylphenyl)-5-methyl-6-(1'-hydroxyethyl)-pen-2-em-3-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1-carba-2-(p-aminomethylphenyl)-5-methyl-6-(1'-hydroxyethyl)-pen-2-em-3-carboxylic acid | 500 mg. |
| Sterile Water | 2 ml. |
| OPTHALMIC SOLUTION | |
| 1-carba-2-(p-aminomethylphenyl)-5-methyl-6-(1'-hydroxyethyl)-pen-2-em-3-carboxylic acid | 100 mg. |
| Hydroxypropylmethylcellulose | 5 mg. |
| Sterile Water to | 1 ml. |
| OTIC SOLUTION | |
| 1-carba-2-(p-aminomethylphenyl)-5-methyl-6-(1'-hydroxyethyl)-pen-2-em-3-carboxylic acid | 100 mg. |
| Benzalkonium Chloride | 0.1 mg. |
| Sterile Water to | 1 ml. |
| TOPICAL OINTMENT | |
| 1-carba-2-(p-aminomethylphenyl)-5-methyl-6-(1'-hydroxyethyl)-pen-2-em-3-carboxylic acid | 100 mg. |
| Polyethylene Glycol 4000 U.S.P. | 400 mg. |
| Polyethylene Glycol 400 U.S.P. | 1.0 gram |

What is claimed is:

1. A compound having the structural formula:

and a pharmaceutically acceptable salt thereof wherein:
$R^1$ is selected from the group consisting of hydrogen, hydroxyloweralkyl and hydroxyloweralkyl substituted by trifluoromethyl;
$R^4$ is selected from the group consisting of loweralkyl, phenyl and benzyl; and
$R^3$ is selected from the group consisting of hydrogen; loweralkyl which may be substituted by hydroxy, amino, formamidino, acetamidino, guanidino, and aminoloweralkyl; and phenyl which may be substituted by loweralkoxy, hydroxyloweralkyl, aminoloweralkyl, and the mono-, di-, and tri-loweralkyl derivatives thereof, formamidinoloweralkyl, acetamidinoloweralkyl, guanidinoloweralkyl and carboxyl.

2. A compound according to claim 1 wherein $R^1$ is selected from the group consisting of Hydrogen, $CH_3CH(OH)-$, $HOCH_2-$, $(CH_3)_2C(OH)-$, $CH_3-CH_2-C(OH)H-$ and $CF_3CH(OH)-$ and $R^3$ is selected from the group consisting of hydrogen, $-CH_2CH_2CH_2NH_2$, $-CH_2CH_2NH_2$, $-CH_3$, $-CH_2CH_2CH_2OH$,

-(C6H4)-OCH3, $-CH_2CH_2CH_2CH_2NH_2$, $-CH_2CH_2CH_2CH_2NH-C(=NH)H$;

$-CH_2CH_2CH_2CH_2NHC(=NH)CH_3$, $-CH_2CH_2CH_2CH_2NHC(=NH)H$, $-CH_2CH_2CH_2NHC(=NH)CH_3$, -(C6H4)-,

-(C6H4)-CH2N(CH3)2, -(C6H4)-COOH,

-(C6H4)-CH2NHCH3, -(C6H4)-CH2NH2,

-(C6H4)-CH2NHCH(CH3)2, -(C6H4)-CH2OH,

-(C6H4)-CH2OH, -(C6H4)-COONa, -(C6H4)-COONa

-(C6H4)-CH2-N=C(H)-NH2, -(C6H4)-CH2-N=C(CH3)-NH2

-(C6H4)-CH2-N(CH3)-C(H)=NH

3. A compound according to claim 2 wherein $R^1$ is H and $R^3$ is H.

4. A compound according to claim 2 wherein $R^1$ is $CH_3-CH(OH)-$ and $R^3$ is H.

5. A compound according to claim 2 wherein $R^1$ is $CH_3-C(OH)(H)-$ and $R^3$ is $CH_2CH_2-CH_2-NH_2$.

6. A compound according to claim 2 wherein $R^1$ is $CF_3-CH(OH)-$ and $R^3$ is H.

7. A compound according to claim 2 wherein $R^1$ is

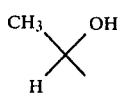

and R³ is

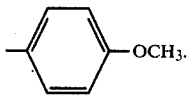

8. A compound according to claim 2 wherein R¹ is

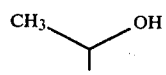

and R³ is

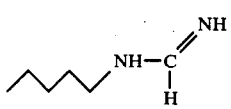

9. A compound according to claim 2 wherein R¹ is

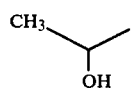

and R³ is

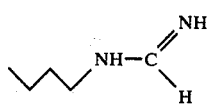

10. A compound according to claim 2 wherein R¹ is

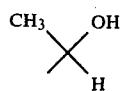

and R³ is

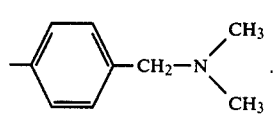

11. A compound according to claim 2 wherein R¹ is

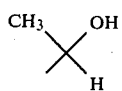

and R³ is

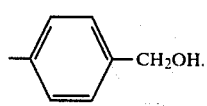

12. A compound according to claim 2 wherein R¹ is

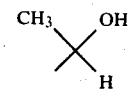

and R³ is

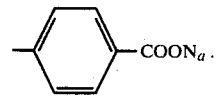

13. A compound according to claim 2 wherein R¹ is

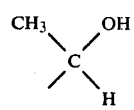

and R³ is

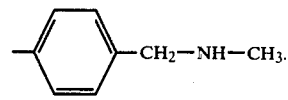

14. A compound according to claim 2 wherein R¹ is

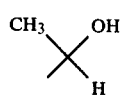

and R³ is

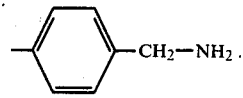

15. A compound according to claim 2 wherein R¹ is

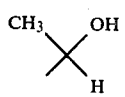

and R³ is

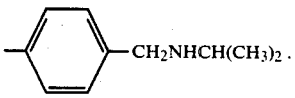

16. A compound according to claim 2 wherein R¹ is

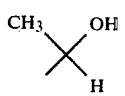

and R³ is

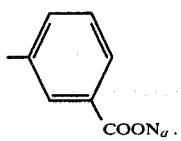

17. A compound according to claim 2 wherein R¹ is

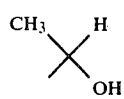

and R³ is

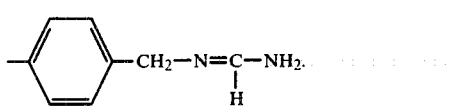

18. A compound according to claim 2 wherein R¹ is —CH₂OH and R³ is

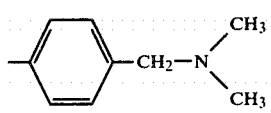

19. A compound according to claim 2 wherein R¹ is —CH₂OH and R³ is

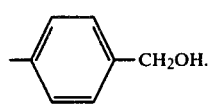

20. A compound according to claim 2 wherein R¹ is —CH₂OH and R³ is

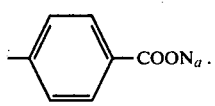

21. A compound according to claim 2 wherein R¹ is —CH₂OH and R³ is

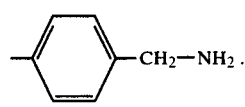

22. A compound according to claim 2 wherein R¹ is —CH₂OH and R³ is

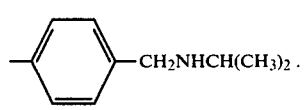

23. A compound according to claim 2 wherein R¹ is —CH₂OH and R³ is

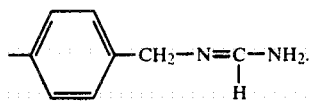

24. A compound according to claim 2 wherein R¹ is

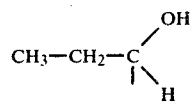

and R³ is

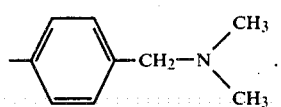

25. A compound according to claim 2 wherein R¹ is

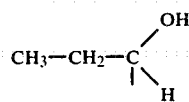

and R³ is

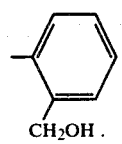

26. A compound according to claim 2 wherein R¹ is

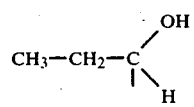

and R³ is

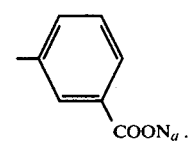

27. A compound according to claim 2 wherein R¹ is

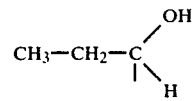

and R³ is

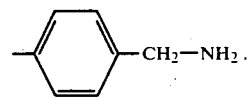

28. A compound according to claim 2 wherein $R^1$ is

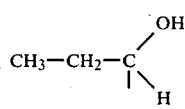

and $R^3$ is

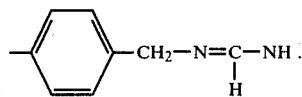

29. A compound according to claim 2 wherein $R^1$ is $CF_3CH(OH)$— and $R^3$ is phenyl.
30. A compound according to claim 2 wherein $R^1$ is $CF_3CH(OH)$— and $R^3$ is

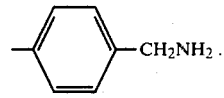

31. A compound according to claim 2 wherein $R^1$ is $CF_3CH(OH)$— and $R^3$ is

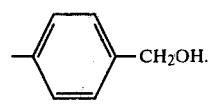

32. An antibiotic pharmaceutical composition comprising a therapeutically effective amount of a compound according to claim 1 and a pharmaceutical carrier therefor.

* * * * *